US005619291A

United States Patent [19]

Putnam

[11] Patent Number: 5,619,291

[45] Date of Patent: Apr. 8, 1997

[54] PATIENT-USER INTERACTIVE PSYCHOTHERAPY APPARATUS AND METHOD

[76] Inventor: Mark D. Putnam, 50 Mission Trail, Woodside, Calif. 94062

[21] Appl. No.: 522,545

[22] Filed: Sep. 1, 1995

[51] Int. Cl.$^{6}$ .................................... A61B 3/02

[52] U.S. Cl. .................... 351/240; 351/239; 351/243; 351/246

[58] Field of Search .......................... 351/237, 238, 351/239, 240, 241, 242, 243, 246, 245

[56] References Cited

U.S. PATENT DOCUMENTS

| | | | |
|---|---|---|---|
| 4,294,522 | 10/1981 | Jacobs | 351/2 |
| 4,346,968 | 8/1982 | Melin et al. | 351/23 |
| 4,421,393 | 12/1983 | Cohen et al. | 351/224 |
| 5,094,521 | 3/1992 | Jolson et al. | 351/210 |
| 5,173,724 | 12/1992 | Bonham et al. | 351/203 |
| 5,214,870 | 6/1993 | Cohen | 40/575 |
| 5,343,261 | 8/1994 | Wilson | 351/203 |
| 5,384,593 | 1/1995 | Gell, Jr. et al. | 348/61 |
| 5,436,681 | 7/1995 | Michaels | 351/239 |

*Primary Examiner*—Hung X. Dang
*Attorney, Agent, or Firm*—Thomas C. Feix; Feix & Feix

[57] ABSTRACT

A patient-user interactive psychotherapy apparatus for use in Eye Movement Desensitization and Reprocessing treatment is disclosed. The psychotherapy apparatus includes a pair of visual displays, each for displaying an image having an emotional impact on a particular patient-user. The visual displays are positioned horizontally spaced from one another in the patient-user's field of view. The visual displays are each operable between two operational states including: a first operational state, wherein the image is highly, visually perceptible by the patient-user; and a second operational state, wherein the image is less visually perceptible by the patient-user. A pair of hand held switch inputs for switching between the two operational states of each visual display is also provided. In use, the patient-user alternately actuates the hand held switch inputs which causes the image to be alternately displayed as a highly, visually perceptible image in a back and forth manner on the two visual displays. The invention allows the patient-user to self-induce a comfortable rate and duration of saccadic eye movement as the patient visually tracks the highly, visually perceptible image displayed on the two visual displays. In accordance with a method aspect of the invention, the patient-user may generate additional competing or distracting input stimulus by incorporating up and down arm movement and actuating the hand held switch inputs by directly physically contacting an actuator mechanism of the switch inputs to parts of their anatomy, such as their knees.

14 Claims, 1 Drawing Sheet

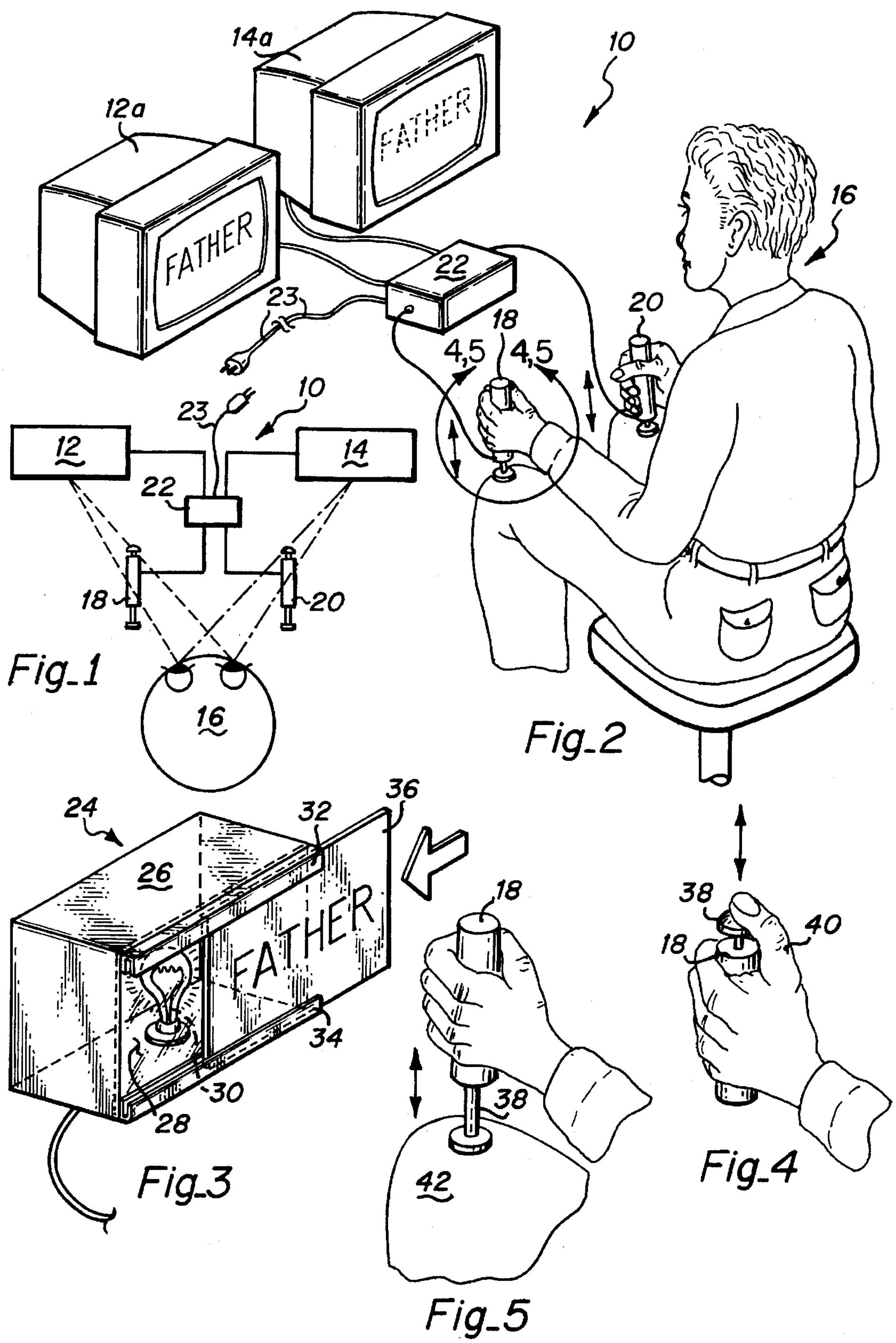
Fig_1
Fig_2
Fig_3
Fig_4
Fig_5

PATIENT-USER INTERACTIVE PSYCHOTHERAPY APPARATUS AND METHOD

FIELD OF THE INVENTION

The present invention relates to an interactive psychotherapy apparatus for providing Eye Movement Desensitization and Reprocessing (EMDR) treatment to a patient-user and a method of use of such interactive psychotherapy apparatus.

BACKGROUND OF THE INVENTION

Eye Movement Desensitization and Reprocessing (EMDR) has recently emerged as one of the hottest trends in clinical psychology. Supporters of EMDR report dramatic results when used as a treatment for patients suffering from Post Traumatic Stress Disorder (PTSD) and other related disorders wherein the patient experiences recurring high levels of anxiety due to the painful and emotional memories associated with a particular traumatic experience or a series of traumatic events which occur over a period of time. Such trauma-based disorders are common to war veterans, rape and assault victims, and survivors of natural disasters, such as earthquakes, fires, hurricanes, and the like.

The EMDR technique is described in a paper by Francine Shapiro, Ph.D., entitled "Eye Movement Desensitization: A New Treatment For Post-Traumatic Stress Disorder", J. Behav. Ther. & Exp. Psychiat. Vol. 20, No. 3, pp. 211–217 (1989). In accordance with the teachings of this paper, the patient is instructed to hold three things in his or her mind including: a single image of the traumatic incident; the associated emotion and body sensation; and the related negative thought. During this time, the patient's eyes visually track the therapist's hand, with two fingers raised, while the hand is swept rhythmically back and forth along the line of vision of the patient. After each set or "saccade" of eye movements, the patient is asked to rate their level of anxiety or other discomfort. It has been found that the above described EMDR technique has been successful in treating cases of PTSD and other trauma disorders.

It is believed that the saccadic eye movements stimulate reprocessing of the traumatic memories and their associated thoughts and feelings by opening up the network of traumatic memories to input from the conscious mind of the patient.

One difficultly encountered by the therapist in administering the EMDR treatment is maintaining a controlled rate of speed and an accurate path of their raised finger's for prolonged time periods, thus resulting in jerky eye movement which may increase, rather than decrease stress in the patient.

Devices are known from the prior an for overcoming the above-described problem. For example, U.S. Pat. No. 5,343,261, issued to Wilson, discloses a device for inducing saccadic eye movement which includes a wand and support structure for holding the wand in a horizontal position within the patient's field of view. The wand is provided with a number of evenly spaced light emitting diodes (LEDs) disposed along its length. In use, the LEDs are turned on and off in linear sequence. This induces saccadic movement of the patient's eyes as the patient visually tracks the sequential back and forth illumination of the LEDs. The wand support structure is provided with height and angle adjustment capability for presetting a desired use position for each new patient.

Wilson's device also includes a separate control mechanism for presetting the rate and duration of the illumination of the LEDs for each treatment session. Wilson's device advantageously relieves the therapist the manual task of moving their hand in a back and forth manner along a controlled path and with even tempo, thereby allowing the therapist to concentrate more on the patient's reactions during the treatment session so that they can better evaluate the effectiveness of the EMDR treatment.

An apparatus which would provide a patient varying degrees of distracting or competing input stimulus, in addition to eye movement stimulus, would be desirable since it could provide more rapid and complete EMDR treatment results. Such distracting or competing input stimulus should preferably assist the patient in holding in their conscience mind an image of the traumatic event or events, the associated emotional and body sensation, and the related negative thought. In this regard, it would be desirable to incorporate visual aids which focus the patient's mental imaging and thought processes during the eye movement stimulus.

Further, it would be desirable to enable a patient to control the rate and duration of his or her eye movement stimulus and other competing or distracting input stimulus during the EMDR treatment and thereby provide increased effectiveness of treatment.

SUMMARY OF THE INVENTION

Briefly, in accordance with a preferred embodiment of the present invention, a psychotherapy apparatus is provided which enables a patient-user to achieve increased effectiveness of the psychotherapy treatment known as Eye Movement Desensitization Reprocessing (EMDR) by providing the patient-user with direct control of the rate and duration of eye movement stimulus during the treatment.

The psychotherapy apparatus of the present invention comprises two visual displays, each for displaying an image having an emotional impact on a particular patient-user. The visual displays are positioned in the patient's field of view and are horizontally spaced from one another. The visual displays are each operable between a first operational state, wherein the image is highly, visually perceptible by the patient-user, and a second operational state, wherein the image is less visually perceptible by the patient-user. The patient-user is provided with a pair of hand held switch inputs, each one being associated with a respective one of the two visual displays. In use, the patient actuates the switch inputs, one at a time, to cause the visual displays to alternate between their two operational states. The patient's eyes visually track the best perceived image which is alternating displayed back and forth on the two visual displays.

In a simple embodiment of the present invention, each of the visual displays comprises light box assembly which includes a box-like container having a display surface formed of a light permeable material, such as frosted glass or color tinted plastic, and which further includes light source disposed within the box-like container. Additional support structure is provided to the perimeter of the display surface which permits for the removable attachment of a sheet of paper or like print media, on which an image is printed or otherwise formed. The particular image that is selected for display is intended to elicit an emotional response from, or is of cognitive importance to the patient-user. The selected image may consist of text, or graphics, or a combination of text and graphics.

In operation, the patient-user actuates one of the hand held switch inputs, which, in turn, activates the light source inside a respective one of the visual displays to create a backlighting effect for the image that is contained on the display surface of the visual display. The backlighting of the displayed image is effective to draw the patient-user's attention to it. In a simple embodiment, the hand held switch inputs comprise simple spring-loaded on/off switches whereby each visual display is activated when its associated switch input is depressed and deactivated when its associated switch input is undepressed. The patient-user is instructed to actuate the switch inputs in an alternating fashion at a rate and duration which is comfortable to the patient-user. The patient-user is also instructed to view the best displayed image that is alternating displayed on the two visual displays. This induces a back and forth or saccadic eye movement in the patient-user at a rate and duration that is determined by the patient-user.

In accordance with an advantageous embodiment of the invention, the visual displays comprise electronically controlled display devices such as television monitors, liquid crystal displays, light emitting diode devices, plasma discharge devices, flat panel displays, and the like. For such electronically controlled displays, additional program means may be employed for on-the-fly generation of additional images for display on the visual displays during an EMDR treatment session.

The hand held switch inputs are preferably linked to a junction box which provides a convenient single housing for joining the cabling for the visual displays and their respective switch inputs as well as a junction to a power cord.

In accordance with one embodiment of the invention, the hand held switch inputs comprise a spring-loaded plunger or trigger mechanism which permits for thumb or finger actuation by the patient-user. It has been found that the additional thumb or finger input stimulus afforded by the hand held switch inputs provide a greater degree of competing or distracting stimulus which is highly effective in countering a fear or anxiety response in the patient-user, thus resulting in more rapid and complete trauma desensitization.

In still yet another advantageous embodiment of the invention, the hand held switch inputs include a plunger-type actuation mechanism which, in use, is orientated in a downward position so that actuation occurs as the patient-user lowers their arm (from an initially raised position) to actuate the switch input by depressing the plunger against their knee. The up and down arm movement along with the plunger-to-knee contact and back and forth eye movement provide an even greater amount of competing or distracting input stimulus to the patient-user for highly effective treatment results.

It is an advantageous feature of the invention to incorporate the alternating display of emotionally charged or cognitively important visual images to the patient-user as part of the eye movement stimulus associated with the conventional EMDR treatment technique. The visual images greatly facilitate the patient-user in holding in their mind an image of the traumatic event as well as the associated emotional or body sensation and negative thought.

Methods and apparatus which incorporate the features described above and which are effective to function as described above constitute specific objects of this invention.

Other and further objects of the present invention will be apparent from the following description and claims and are illustrated in the accompanying drawings, which by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the an without departing from the present invention and the purview of the appended claims.

BRIEF DESCRIPTION OF THE DRAWINGS

FIG. 1 is a schematic view showing the relationship of the psychotherapy apparatus of the present invention and the saccadic eye movement of a patient-user.

FIG. 2 is an isometric view of the psychotherapy apparatus of the present invention in use with a patient-user.

FIG. 3 is an isometric view of a visual image display assembly constructed in accordance with one embodiment of the present invention.

FIG. 4 is an enlarged view of the portion of FIG. 2 shown encircled by arrows 4—4 which illustrates a patient-user actuated switch input mechanism and method of use in accordance with one embodiment of the present invention.

FIG. 5 is an enlarged view of the portion of FIG. 2 shown encircled by arrows 5—5 which illustrates a patient-user actuated switch input mechanism and method of use in accordance with a second embodiment of the present invention.

DETAILED DESCRIPTION OF THE INVENTION

A psychotherapy apparatus which enables a patient-user to self induce a controlled rate and duration of saccadic eye movement for use in Eye Movement Desensitization and Reprocessing (EMDR) treatment is designated generally by reference numeral 10 in FIG. 1.

The psychotherapy apparatus 10 includes two visual displays 12 and 14 which are spaced apart from one another and are positioned within the field of view of a patient user 16. The visual displays 12, 14 are connected via junction box 22 to a pair of hand held patient-user actuated switch inputs 18 and 20.

The purpose and function of the visual displays 12, 14 is to display a visual image to the patient-user. The particular image that is to be displayed on the visual displays 12, 14 is selected to have some emotional significance or cognitive importance that is related to the condition for which the particular patient-user is seeking psychotherapy treatment. The emotional material for use as the displayed image may, as an example, include text, graphics, or a combination thereof.

Each visual display 12, 14 is operable between a first and a second operational state. In the first operational state, the displayed image is illuminated or is otherwise made more pronounced such that it is highly, visually perceptible by the patient-user 16. In the second operational state, the visual display is dimmed or is completely deactivated such that the displayed image is less visually perceptible by the patient-user. The idea is that the patient-user is instructed to visually track the highly, visually perceptible image as it is being alternately displayed on the two visual display 12, 14 thereby inducing a back and forth or saccadic eye movement in the patient-user 16.

Each of the hand held switch inputs 18 and 20 controls the activation and deactivation of a respective one of the visual displays 12 and 14 between their first and second operational states. The switch inputs preferably comprise spring loaded actuator mechanisms which function to send or cut voltage to its respective visual display when depressed or released. A junction box 22 provides a convenient single housing for joining a single power cord to the cabling associated with the visual displays 12, 14 and their respective switch inputs 18, 20.

When the patient-user 16 actuates the left switch input 18, an activation signal is sent to the left visual display 12 whereby the displayed image is illuminated or is made highly, visually perceptible. To deactivate the left visual display 12, the patient-user simply releases pressure on the actuator mechanism of the left switch input 18, whereby the displayed image is dimmed or is made less visually perceptible. Similarly, when the patient-user 16 actuates the right switch input 20, an activation signal is sent to activate the right visual display 14, whereby the displayed image is illuminated or is made highly, visually perceptible. Again, to deactivate the right visual display 14, the patient-user simply releases pressure on the actuator mechanism of the right switch input 20, whereby the displayed image is dimmed or is made less visually perceptible.

The hand held switch inputs 18 and 20 advantageously enable a patient-user to control the tempo and duration of back and forth eye movement. I have found that by providing the patient with such self control over their eye movement, the patient tends to be more comfortable during the EMDR treatment session and more rapid and complete therapeutic results can be achieved.

FIG. 2 shows one embodiment of the present invention wherein the visual displays comprise conventional electronically controlled Cathode Ray Tube (CRT) displays 12*a* and 14*a*. It is understood that any number of different devices can be used for the two visual displays, including, but not limited to, television monitors, liquid crystal displays, light emitting diode devices, plasma discharge devices, flat panel displays, and the like.

It may also be advantageous to use a computer (not shown) to generate a number of images which may be displayed to the patient-user 16 over the course of a treatment session.

A visual display constructed in accordance with a simple low cost embodiment of the present invention is indicated generally by reference numeral 24 in FIG. 3.

In this embodiment, the visual display 24 is constructed as a light box assembly including a box-like housing 26 having a light permeable display surface 28, which is oriented to face the patient-user, and an interiorly disposed light source 30. The perimeter of the display surface 28 is provided with support structure, e.g. upper and lower transverse slotted guide members 32 and 34, designed to removably secure print media 36 (e.g. a piece or paper or plastic film) bearing an image of emotional impact immediately adjacent the display surface 28. The display surface 28 preferably comprises frosted glass, color tinted plastic or like material which provides a desired backlighting effect for the displayed image on the print media 36 when the light source 28 is activated.

FIGS. 4–5 show alternate embodiments for and methods of use of the hand held patient-user actuated switch inputs of the present invention.

FIG. 4 shows a switch input 18 being held by the left hand of a patient-user. The switch input 18 includes a plunger mechanism 38 which is oriented in an upward position for convenient actuation by the user's thumb 40. An obvious variation of this embodiment would include a trigger mechanism for actuation by the user's finger(s) much like a spray trigger on a plastic spray bottle or a trigger mechanism on a joy stick.

FIG. 5 shows the switch input 18 oriented in a reverse position such that the plunger mechanism 38 points downward. In use, the patient-user swings their arms in an up and down manner so that actuation of the switch input 18 occurs as the plunger 38 is depressed against the patient-user's knee 42, which, in ram, activates a respective one of the visual displays. The up and down arm movement, along with the plunger-to-knee contact provide a greater degree of competing or distracting stimulus to the patient user than is possible by the "eye movement-only" stimulus devices and treatment techniques of the prior art.

As can be readily appreciated by those of ordinary skill in the art, the patient-user may use the various actuation methodologies described above in order to select a desired and effective amount of additional competing or distracting input stimulus for any particular treatment session. Further, the switch inputs of the present invention allow the patient-user, and not the therapist, to regulate the rate and duration of the input stimulus, thus eliminating possible stress to the patient which could otherwise occur if the therapist were to maintain sole control over the input stimulus to the patient. In most cases, the patient is best able to determine what a comfortable rate and duration of input stimulus. Of course, not everyone responds to input stimulus in the same way. In such situations, it may be preferred that the therapist assume control of the actuation of the switch inputs. Alternatively, actuation of the switch inputs could be automated including the provision of independent control means for regulating the rate, tempo and/or duration of the activation and deactivation of the visual displays.

It should be understood that various modifications within the scope of this invention can be made by one of ordinary skill in the art without departing from the spirit thereof. I therefore wish my invention to be defined by the scope of the appended claims as broadly as the prior art will permit, and in view of the specification if need be.

What is claimed is:

1. A patient-user interactive psychotherapy apparatus comprising:

a) a pair of separate and mutually distinct visual display means, each for displaying an image having an emotional impact on a particular patient-user, said pair of visual display means being positioned horizontally spaced from one another in the patient-user's field of view at a distance sufficiently far apart from one another to induce saccadic eye movement in the patient user as the patient-user alternately views each of said visual display means, each of said visual display means being operable between two operational states including:

i) a first operational state wherein the image is highly, visually perceptible by the patient-user;

ii) a second operational state wherein the image is less visually perceptible by the patient-user; and b) left and fight switch input means actuable by left and right hands of the patient user for alternatingly actuating said pair of visual display means between said first and second operational states to permit the patient-user to self-induce a comfortable rate and duration of saccadic eye movement as the patient visually tracks the image as it is alternatingly displayed as a highly visually perceptible image on the two visual display means.

2. The invention as recited in claim 1, wherein said switch input means comprises:

a) a pair of hand held switch units; and b) each of said hand held switch units having a spring-loaded actuator mechanism which is effective to activate a respective visual display means when depressed and deactivate a respective visual display means when undepressed.

3. The invention as recited in claim 2, wherein each of said visual display means comprises an illuminated sign assembly which includes:

a) a display surface formed of a light permeable material;

b) a sheet of print media containing an image;

c) support means for removably securing said sheet of print media and image to said display surface; and d) a light source responsive to said switch input means and disposed behind said display surface to provide a backlit effect on said image when said light source is turned on.

4. The invention as recited in claim 1, wherein each of said visual display means comprises an illuminated sign assembly which includes:

a) a display surface formed of a light permeable material;

b) a sheet of print media containing an image;

c) support means for removably securing said sheet of print media and image to said display surface; and d) a light source responsive to said switch input means and disposed behind said display surface to provide a backlit effect on said image when said light source is turned on.

5. A patient-user interactive psychotherapy apparatus comprising:

a) a pair of separate and mutually distinct visual displays, each for displaying an image having an emotional impact on a particular patient-user, said pair of visual displays being positioned horizontally spaced from one another in the patient-user's field of view at a distance sufficiently far apart from one another to induce saccadic eye movement in the patient-user as the patient-User alternately views each of said visual display means, each of said visual displays being operable between two operational states including:

i) a first operational state wherein the image is highly, visually perceptible by the patient-user;

ii) a second operational state wherein the image is less visually perceptible by the patient-user; and b) a left and right hand pair of switch inputs actuable by left and right hands of the patient user for alternatingly actuating said pair of visual displays between said first and second operational states to permit the patient-user to self-induce a comfortable rate and duration of saccadic eye movement as the patient visually tracks the image as it is alternatingly displayed as a highly, visually perceptible image on the two visual displays.

6. The invention as recited in claim 5, wherein each of said switch inputs comprises a hand held switching unit, and wherein each hand held switch unit includes a spring-loaded actuator mechanism which is effective to activate a respective visual display when depressed and deactivate a respective visual display when undepressed.

7. The invention as recited in claim 6, wherein each of said visual displays comprises an illuminated sign assembly which includes:

a) a display surface formed of a light permeable material;

b) a sheet of print media having an image contained thereon;

c) support structure for removably securing said sheet of print media and image to said display surface; and d) a light source responsive to a respective switching unit, said light source disposed behind said display surface to provide a backlit effect on said image when said light source is turned on.

8. The invention as recited in claim 5, wherein each of said visual displays comprises an illuminated sign assembly which includes:

a) a display surface formed of a light permeable material;

b) a sheet of print media having an image contained thereon;

c) support structure for removably securing said sheet of print media and image to said display surface; and d) a light source responsive to a respective switching unit, said light source disposed behind said display surface to provide a backlit effect on said image when said light source is turned on.

9. A patient-interactive method for inducing saccadic eye movement in the patient for use in psychological therapy and treatment of emotional traumas of the patient, comprising the step of:

a) positioning a patient in front of first and second visual image displays, said first and second visual image displays being positioned at eye level and being spaced apart from one another such that they are positioned at substantially opposing end regions of a saccadic eye movement range of the patient;

b) providing first and second patient-actuable switch inputs for controlling the respective actuation of said first and second visual image displays; and c) alternately displaying an emotional charged image on one of said first and second visual image displays in response to patient actuation of a respective one of said first and second switch inputs such that a patient-controlled rate or saccadic eye movement is achieved as the patient views the alternately displayed emotionally charged images on said first and second visual image displays.

10. The invention as recited in claim 9 wherein the patient-actuable switch inputs each include a plunger-type actuation mechanism and wherein the invention includes the step of actuating a respective one of the switch inputs by having the patient raise and lower an arm holding a switch input in order to depress its associated plunger mechanism against their knee to provide the patient with additional competing or distracting input stimulus.

11. A patient-user interactive psychotherapy apparatus comprising:

a) a pair of visual display means, each for displaying an image having an emotional impact on a particular patient-user, said pair of visual display means being positioned horizontally spaced from one another in the patient-user's field of view, each of said visual display means being operable between two operational states including:

i) a first operational state wherein the image is highly, visually perceptible by the patient-user;

ii) a second operational state wherein the image is less visually perceptible by the patient-user;

b) switch input means actuable by the patient user for alternatingly actuating said pair of visual display means between said first and second operational states to permit the patient-user to self-induce a comfortable rate and duration of saccadic eye movement as the patient visually tracks the image as it is alternatingly displayed as a highly visually perceptible image on the two visual display means; and wherein c) each of said visual display means comprises an illuminated sign assembly including:

i) a display surface formed of a light permeable material;

ii) a sheet of print media containing said image;

i) support means for removably securing said sheet of print media and image to said display surface; and iv) a light source responsive to said switch input means and disposed behind said display surface to provide a backlit effect on said image when said light source is turned on.

12. The invention as recited in claim 11, wherein said switch input means comprises:

a) a pair of hand held switch units; and b) each of said hand held switch units having a spring-loaded actuator mechanism which is effective to activate a respective visual display means when depressed and deactivate a respective visual display means when undepressed.

13. A patient-user interactive psychotherapy apparatus comprising:

a) a pair of visual displays, each for displaying an image having an emotional impact on a particular patient-user, said pair of visual displays being positioned horizontally spaced from one another in the patient-user's field of view, each of said visual displays being operable between two operational states including:

i) a first operational state wherein the image is highly, visually perceptible by the patient-user;

ii) a second operational state wherein the image is less visually perceptible by the patient-user;

b) a pair of switch inputs actuable by the patient user for alternatingly actuating said pair of visual displays between said first and second operational states to permit the patient-user to self-induce a comfortable rate and duration of saccadic eye movement as the patient visually tracks the image as it is alternatingly displayed as a highly, visually perceptible image on the two visual displays; and wherein:

c) each of said visual displays comprises an illuminated sign assembly which includes:

i) a display surface formed of a light permeable material;

ii) a sheet of print media having an image contained thereon;

iii) support structure for removably securing said sheet of print media and image to said display surface; and iv) a light source responsive to a respective switching unit, said light source disposed behind said display surface to provide a backlit effect on said image when said light source is turned on.

14. The invention as recited in claim 13, wherein each of said switch inputs comprises a hand held switching unit, and wherein each hand held switch unit includes a spring-loaded actuator mechanism which is effective to activate a respective visual display when depressed and deactivate a respective visual display when undepressed.

* * * * *